United States Patent [19]

Hildenbrand et al.

[11] Patent Number: 5,412,811
[45] Date of Patent: May 9, 1995

[54] HEADGEAR HAVING A HOLDING DEVICE FOR HOLDING AN INSTRUMENT

[75] Inventors: Peter Hildenbrand, Beimerstetten; Walter Matuschek, Aalen; Heinz Gottlob, Königsbronn, all of Germany

[73] Assignee: Carl-Zeiss-Stiftung, Heidenheim, Germany

[21] Appl. No.: 955,976

[22] Filed: Oct. 2, 1992

[30] Foreign Application Priority Data

Oct. 4, 1991 [DE] Germany ............. 91 12 375 U
Oct. 4, 1991 [DE] Germany ............. 91 12 376 U
Oct. 4, 1991 [DE] Germany ............. 91 12 377 U

[51] Int. Cl.⁶ ............................................. A42B 3/04
[52] U.S. Cl. ........................................ 2/10; 2/417; 2/418; 351/156
[58] Field of Search ........... 2/10, 417, 418, 419, 2/420, 422, 6, 6.3, 6.5, 6.7; 351/155, 156, 205; 128/23; 248/186, 289.1; 359/409, 410, 411; 602/16

[56] References Cited

U.S. PATENT DOCUMENTS

| 1,671,342 | 5/1928 | Cantor ............................. 2/10 |
| 2,205,741 | 6/1940 | Bowers ........................... 2/418 |
| 2,757,574 | 8/1956 | Thorburn ..................... 351/156 |
| 2,926,406 | 3/1960 | Edwards ........................ 2/418 |
| 2,983,923 | 5/1961 | Aileo ............................... 2/418 |
| 3,439,672 | 4/1969 | Fisher ........................... 602/16 |
| 3,830,230 | 8/1974 | Chester .......................... 128/23 |
| 3,963,329 | 6/1976 | Stumpf et al. ................ 351/205 |
| 4,170,792 | 10/1979 | Higgs ............................... 2/6.5 |
| 4,468,817 | 9/1984 | Nunnery .................... 2/DIG. 11 |
| 4,593,683 | 6/1986 | Blaha ............................. 128/23 |
| 4,681,413 | 7/1987 | Schmidt et al. .............. 351/205 |
| 4,942,628 | 7/1990 | Freund ............................ 2/417 |
| 5,077,836 | 1/1992 | Idoff ............................... 2/417 |

FOREIGN PATENT DOCUMENTS

3516581 11/1986 Germany.
2123166 1/1984 United Kingdom.
WO89/02202 3/1989 WIPO.

*Primary Examiner*—Clifford D. Crowder
*Assistant Examiner*—Diana L. Biefeld
*Attorney, Agent, or Firm*—Walter Ottesen

[57] ABSTRACT

The invention is directed to a headgear with a holding device for a measuring unit, illuminating unit or viewing unit. The headgear has a headband and a frontal band and is mounted on the head of the wearer of the headgear. A base body is mounted on the frontal band and a bracket for holding the unit is attached to said base body by a clamping device. The clamping device is manually actuable between a fixing position wherein the bracket is movably fixed relative to the base body and a releasing position wherein the bracket is released so as to permit movement of the bracket in elevation relative to the base body. A detent device permits the bracket to be rotated relative to the base body while the clamping device is in the fixing position.

25 Claims, 5 Drawing Sheets

HEADGEAR HAVING A HOLDING DEVICE FOR HOLDING AN INSTRUMENT

FIELD OF THE INVENTION

The invention relates to a headgear having a holding device for an instrument such as a measuring unit, illuminating unit or viewing unit. The headgear includes a headband and a frontal band as well as a device for changing the length of the frontal band.

BACKGROUND OF THE INVENTION

A headgear of the above type permits apparatus to be mounted on the head of a user so that the hands are free for work and so that the apparatus is always in front of the eyes of the user during work. A wide area of application of the headgear is therefore microsurgery, dentistry and ophthalmology.

The headgear available in the marketplace are equipped with inner padding made of plastic, foam or leather. The formation of sweat by the wearer of the headgear and moisture collecting beneath these paddings is problematic with all these materials.

U.S. Pat. No. 4,593,683 discloses a headgear having a viewing unit and an illuminating unit wherein the headgear is open at the occipital end. The open ends are slideable one over the other for adjusting the diameter of the headgear and are held together by means of a clamping screw. This clamping screw is configured as a counterweight for the viewing unit and the illuminating unit.

German Patent 3,516,581 discloses a headgear characterized as a headband with at least one removable pad on at least one segment of the headgear. Here, the padding is made of a material which is elastically stable as to form and has a strap profile which engages in a hooklike manner over the periphery of the headgear and is latched thereto.

Published United Kingdom patent application 2,123,166 (corresponding to United States patent application Ser. No. 391,494, filed Jun. 24, 1982) and U.S. Pat. No. 3,963,329 disclose a headgear characterized as a head frame and having an adjusting device for the frontal band for adjusting to the individual head circumference. The headgear also has a headband.

U.S. Pat. Nos. 3,963,329 and 4,593,683 as well as published United Kingdom patent application 2,123,166 all show a headgear having a holding device at the frontal end thereof for holding a viewing unit.

SUMMARY OF THE INVENTION

It is an object of the invention to provide a headgear which facilitates an individual use of an illuminating unit or viewing unit on the headgear while at the same time being comfortable for the wearer.

The headgear of the invention is to be worn on the head and adapted for holding a measuring unit, illuminating unit or viewing unit and includes: a frontal band extending around the circumference of the head of the wearer and having a front end portion; a headband extending over the head of the wearer and having respective headband ends connected to the frontal band; a base body mounted on the front end portion; a bracket for holding the unit; clamping means manually actuable between a fixing position wherein the bracket is immovably fixed relative to the base body and a releasing position wherein the bracket is released so as to permit movement of the bracket relative to the base body; translation means for permitting the bracket and the unit to be moved in elevation along a predetermined line of movement relative to the base body so long as the clamping means is in the releasing position; and, detent means for permitting the bracket to be rotated along a predetermined second line of movement relative to the base body while the clamping means is in the fixing position.

The arrangement of the bracket on the headgear enables the mounted apparatus to be easily adjusted individually in accordance with the requirements of the wearer without reducing the comfort of wearing the headgear.

The frontal band is advantageously adjusted with respect to its length which is a positive contribution to wearing comfort.

The movability of the headband permits the wearer to keep the headband on the head where it is most comfortable for the wearer and the measuring unit, illuminating unit or viewing unit is provided with the largest possible hold on the headgear by means of the headband.

This pleasant wearer comfort and the reliable seating of the headgear on the head is supported in an advantageous manner by making the frontal band in two parts whereby the rearward frontal-band segment can come into contact with the neck region of the wearer. The frontal band and/or the headband are configured in an advantageous manner so as to be changeable in length.

The headband of the invention permits a simple individual adaptation of the headgear to the head of the wearer. The headband has two ends which are movably attached via connecting elements to the frontal band.

A protective cap on the measuring unit, illuminating unit or viewing unit prevents a contamination thereof when the headgear is on the head of the wearer.

A rapid exchange of the apparatus is ensured by the clamping attachment as well as the easy adaptation to different wearers of the headgear.

Mounting the apparatus to a special holding device ensures an optimal position change of the apparatus relative to the viewing axes of the eyes of the wearer.

The bracket, on which the apparatus such as a measuring unit, illuminating unit or viewing unit is attached, is rotatably journalled on the base body by means of a latch hold in order to permit a short reliable shift of the apparatus away from in front of the eyes of the wearer without it being necessary to remove the apparatus.

At least one padding unit is provided in the inner region of the headgear in order to ensure comfort while wearing the headgear. The padding can be in the frontal, occipital or parietal region of the wearer.

The padding attached to the headgear absorbs the sweat of the wearer thereof and thereby prevents moisture from collecting and in this way ensures that during a longer wearing period of the headgear, the sweat emanating at the locations of contact of the headgear on the head of the wearer does not affect comfort. The easy removal also ensures that for a padding soaked with sweat, a hygienic condition is obtained quickly, also when there is an exchange of wearers of the headgear.

Furthermore, the easy removability of the padding permits the headgear to be completely disinfected when used in the medicine. The easy removability of the padding is obtained in an advantageous manner in that the padding is attached by means of a VELCRO band on the headgear.

The surface casing should be made of a water permeable material to facilitate absorbing sweat. Such a material can be polypropylene or a mixed fabric having similar characteristics. The material itself should be compatible with the skin but reject water. All other water permeable materials are suitable which are resistant to tearing such as the materials recited above and which are also compatible with the skin.

In the padding, at least one further material is applied in an advantageous manner to the surface casing which absorbs moisture extremely well (for example, viscose needlefelt, cotton or a material having correspondingly good moisture absorbing characteristics).

The padding lies on the head of the head-gear wearer with the largest surface possible by placing the padding on a carrier which is elastically bendable and located in the forehead area, neck area and/or skull cap area.

Padding on the occipital and/or frontal region of the frontal band and/or on the headband substantially increase the wearing comfort of the headgear.

Attaching the rearward padding to a carrier which is elastically bendable achieves an optimal positioning of the padding. This carrier is advantageously attached to the adjusting receptacle in order to ensure an optimal seating of the padding for every head circumference.

BRIEF DESCRIPTION OF THE DRAWINGS

The invention will now be described with reference to the drawings wherein.

DESCRIPTION OF THE PREFERRED EMBODIMENT OF THE INVENTION

Figure 1:
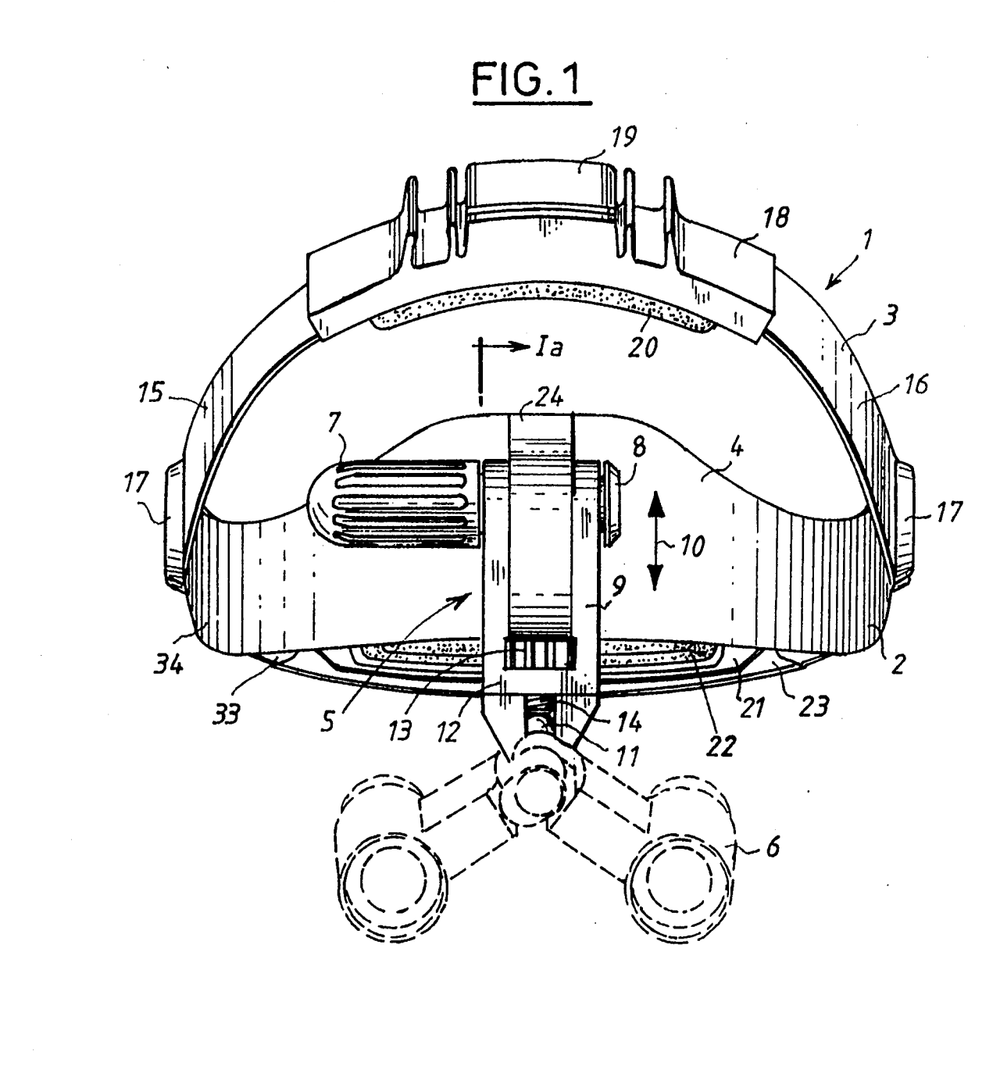
FIG. 1 is a front elevation view of the headgear according to the invention.

The headgear 1 shown in FIG. 1 has a frontal band 2 and a headband 3 which go on the head of a user. Both bands (2, 3) are made of a flexible hard plastic material which is easy to clean and easy to disinfect. The frontal band 2 has a widening 4 at its forward facing portion on which a holding device 5 for a viewing unit 6 is mounted. The viewing unit 6 can, for example, be a prism magnifier as shown in FIG. 1.

This holding device 5 comprises a stable base body 24 on which a rotatable bracket 9 is mounted with an adjusting knob 7 and a clamping screw 8. The bracket 9 is mounted so as to be adjustable in elevation along the movement line 10. A holding device for an optical viewing unit 6 is disposed on this bracket 9.

The base body 24 as well as the bracket 9, the adjusting knob 7 and the clamping screw 8 all have a surface (for example plastic) which is easy to disinfect.

The viewing unit 6 has a spherical-head extension 11 (for example made of steel) which is seated in a cavity formed in a corresponding manner and located in the end region 12 of the bracket 9 when attaching to the bracket 9. In this cavity, the spherical-head extension 11 is fixed in its position by means of a threaded bolt 14 disposed on a fixing gear 13. The threaded bolt 14 then passes through a threaded bore (not shown) in the end region 12 of the bracket 9. When the bolt 14 is loosened by means of the fixing gear 13, then the viewing unit 6 can be moved on a spherical surface having a center point in the sphere of the spherical-head extension 11 and the selected position of the viewing unit 6 is fixed by tightening the bolt 14 by means of the fixing gear 13. All edges on the holding device 5 are rounded in order to minimize the danger of injury.

The headband 3 is in two parts with each of the two headband parts (15, 16) being connected to the forward part 34 of the frontal band 2 by means of a connecting element 17 so as to be movable in such a manner that a movement of the headband 3 is possible along the movement line 56 (FIG. 3) from the forehead to the back of the head of the wearer of the headgear. The two other band ends of the headband parts (15, 16) project into an adjusting receptacle 18. This adjusting receptacle 18 is only open on the side for the insertion of the band ends of the headband parts (15, 16) and otherwise encloses the headband parts (15, 16) completely. A slider 19 is located on the upper central portion of the adjusting receptacle 18. The headband parts (15, 16) in the adjusting receptacle 18 are loosened by pushing the slider 19 in the viewing direction of the wearer and the headband 3 can then be made wider. If the headgear 1 is on the head of the wearer, then the headband parts (15, 16) are latchingly inserted into the adjusting receptacle 18 in accordance with the state of the art in order to adapt a headband which is too large to the head of the wearer.

A padding 20 is provided below the adjusting receptacle 18 in order to ensure comfortable wearing of the headgear 1.

The frontal band 2 has a carrier 21 which is elastically bendable on the inner side and a further padding 22 is provided on this carrier 21. The carrier 21 is located at the rearward end of the frontal band 2 in the region of the back of the head of the wearer. This carrier 21 is mounted on the adjusting receptacle 23 of the frontal band 2 and is explained in greater detail with respect to FIG. 2.

Figure 1A:
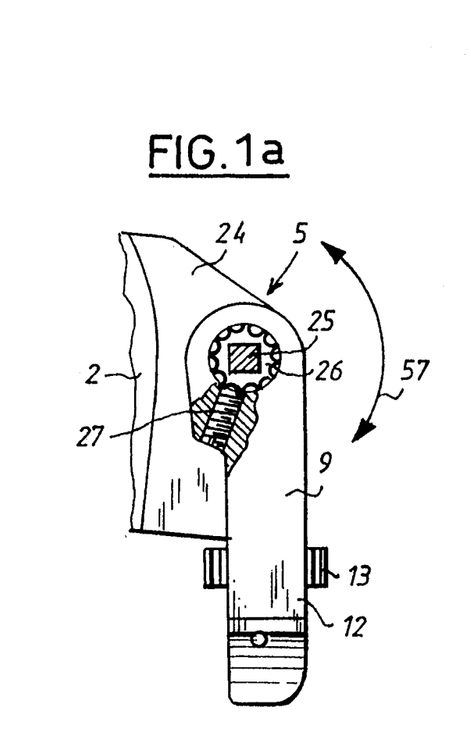
FIG. 1a is a detail view of the pivot mechanic of the attachment device of the headgear of FIG. 1.

The latching pivot mechanics of the holding device 5 are shown in FIG. 1a. In the region of the bracket 9, a steel pin 25 has a quadratic cross section at the clamping screw 8. A detent disc 26 is arranged around the steel pin 25 on both sides of the bracket 9. The detent positions are fixed by a spring-biased pressure piece 27. The force for changing from one detent position to the next is set by rotating this pressure piece 27 in or out with the bracket 9 moving along the direction of double arrow 57.

Figure 2:
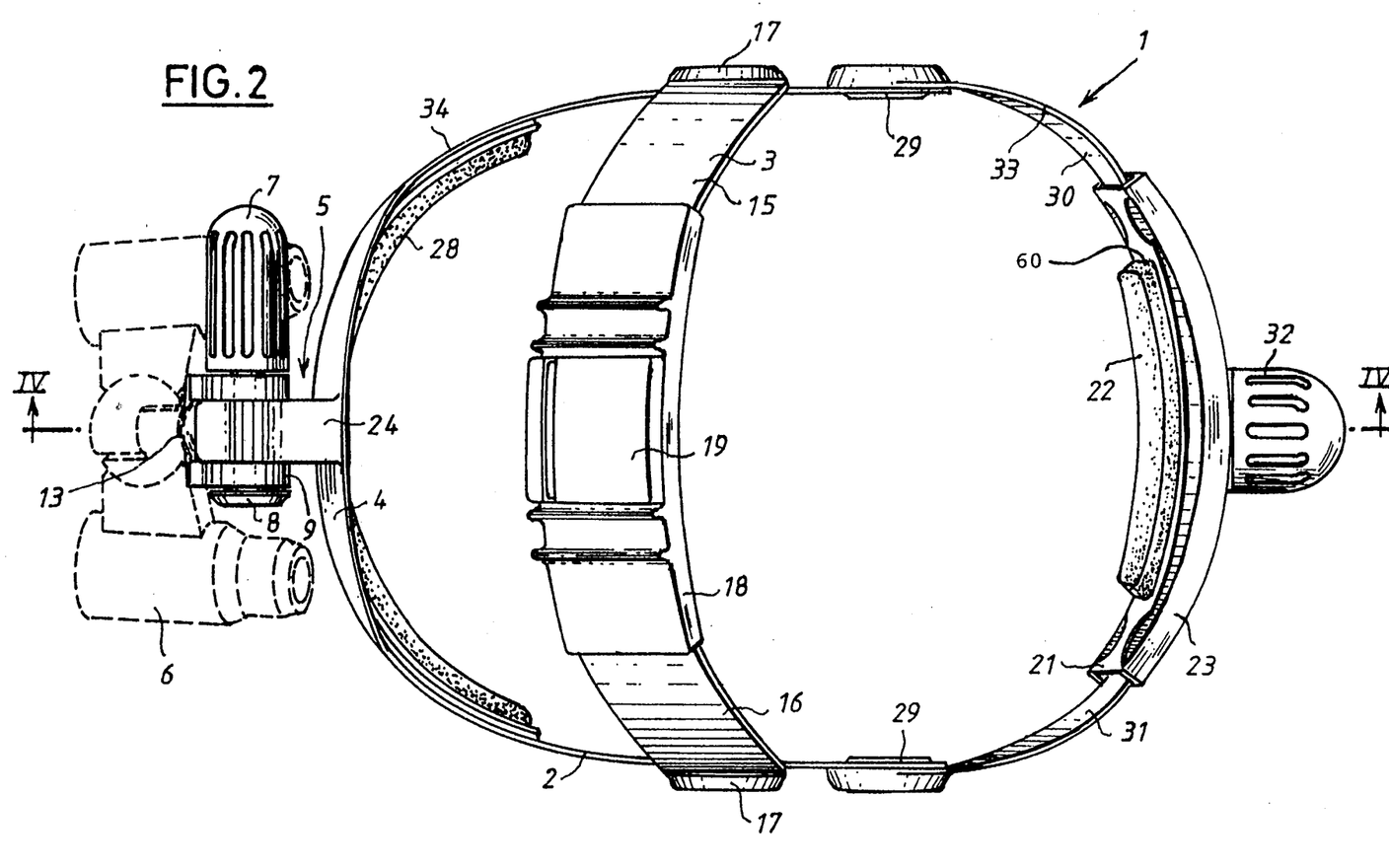
FIG. 2 is a plan view of the headgear of FIG. 1.

The headgear 1 is shown in plan view in FIG. 2. The frontal band 2 has padding 28 on the forehead end and padding 22 at the occipital end. The two parts (15, 16) of the headband 3 are connected at their respective ends to the frontal band 2 by means of respective connecting elements 17. The headband 3 is lengthened by displacing the slider 19 in the direction toward the viewing unit 6. The headband 3 is shortened by pushing the headband parts (15, 16) into the adjusting receptacle 18.

The holding device 5 includes base body 24, bracket 9, adjusting knob 7, clamping screw 8 and fixing gear 13 and is mounted on the band widening 4 of the forward segment 34 of the frontal band. This holding device 5 is explained in greater detail with respect to FIG. 4.

The forward segment 34 and the rearward segment 33 of the frontal band are connected to each other at both ends by respective connecting elements 29. These connecting elements 29 correspond in their configuration to the connecting element 17 and are explained in greater detail with respect to FIG. 3a.

The adjusting receptacle 23 is located on the rearward segment 33 of the frontal band wherein the frontal band 2 is adapted to the head circumference of the wearer by rotating the fixing screw 32. In order to make this length adaptation possible, the rearward frontal-band segment 33 comprises two parts (30, 31). The rearward padding 22 is mounted on a carrier 21 which is elastically bendable and which is attached to the adjusting receptacle 23 at its ends.

Figures 3, 3A:
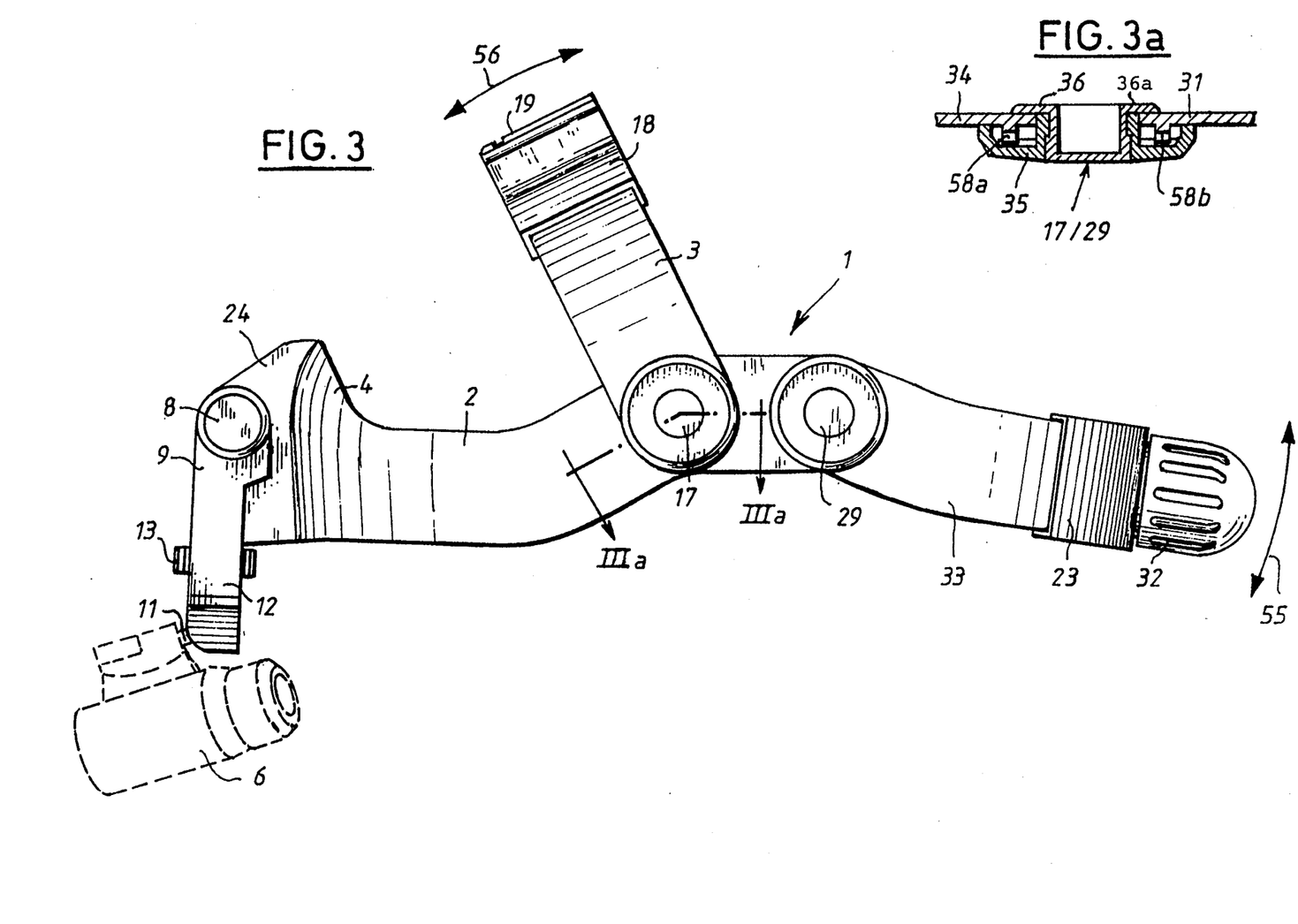
FIG. 3 is a side elevation view of the headgear of FIG. 1.
FIG. 3a is a detail view of a connecting element between the forward and rearward parts of the headgear of FIG. 4.

The side elevation view of the headgear 1 in FIG. 3 shows the ergonomically favorable configuration of the headgear 1. The headgear 1 has a band widening 4 in the forehead region of the carrier in order to ensure a reliable mounting of the viewing unit 6. The frontal band 2 is guided slightly upwardly in the region of the temples of the wearer so that the ears of the wearer are not disturbed by the headgear 1. The headgear 1 is configured so as to be straight above the ears of the wearer. The rearward frontal-band segment 33 is mounted to the connecting element 29. This rearward frontal-band segment 33 can be moved upwardly or downwardly in the direction of double arrow 55 so that the headgear 1 can be optimally positioned with respect to wearing comfort and safety. The adaptation of the length of the headband 3 and the frontal band 2 takes place with the alignment of the frontal band 2 in the respective adjusting receptacles (18, 23).

FIG. 3a shows a simple but very reliable construction of the connecting elements (17, 29) of the frontal band attachment. Risers (58a, 58b) are formed on the ends of the forward frontal-band segment 34 and the rearward frontal-band segment 31, respectively. These risers (58a, 58b) engage into corresponding radial cutouts of an outer cover 35 of the connecting element 29. An inner cover 36 is clipped into the outer cover 35 for fixing this outer cover 35. The inner cover 36 has a long radially-shaped flange 36a at its free outer end. This flange 36a ensures that the frontal-band segments (34, 31) do not slide out of the connecting element 29. The connecting element 17 for the attachment of the headband 3 to the frontal band 2 is correspondingly configured. These connecting elements (17, 29) permit a reliable permanent and yet cost-effective connection between plastic parts of limited elasticity.

Figure 4:
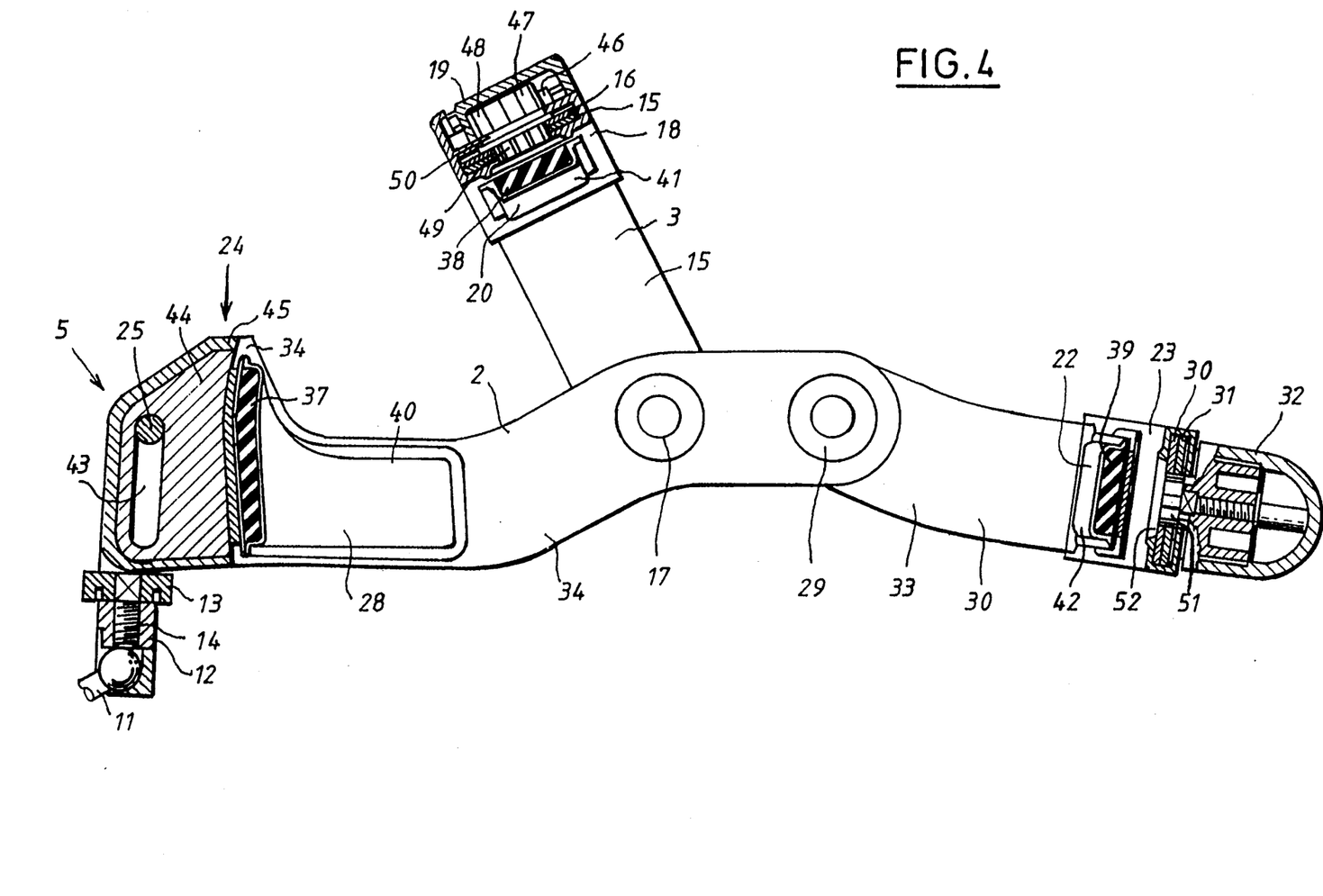
FIG. 4 is a side elevation section view taken along line IV—IV of FIG. 2.

The cross section of FIG. 4 clearly shows the configuration of the adjusting receptacle (18, 23) and the inner configuration of the holding device 5.

The holding device 5 is mounted on the forward frontal-band segment 34 and comprises the base body 24 which, in turn, comprises an inner body 44 (made, for example, of a light metal or plastic reinforced with glass fibers) having a thick hard-plastic casing 45. A slot 43 is provided in the base body 24 in which a steel pin 25 as an extension of the clamping screw 8 is limited in its space for movement. An adjusting knob 7 (FIG. 2) is attached via a winding (not shown) to this steel pin 25. The bracket 9 is disposed between the adjusting knob 7 and the clamping screw 8 (FIG. 2) laterally about the base body 24. The bracket 9 can, for example, be made of aluminum and has a slot through which the steel pin 25 extends with the steel pin being on the clamping screw 8.

The adjusting knob 7 and the clamping screw 8 effect a clamping force and if this clamping force is reduced by means of the adjusting knob 7, then the bracket 9 can be displaced relative to the base body 24 in the vertical direction. When the viewing unit 6 has the proper position in elevation relative to the eyes of the user, then the vertical relative position of the bracket 9 to the base body 24 can be fixed by turning tight the adjusting knob 7. The vertical displacement is here limited by the slot 43.

The adjusting knob 7 is protected from becoming separated from the thread of the steel pin 25 so that, for a change of the vertical position in elevation of the viewing unit 6, the danger is never present that the viewing unit 6 could become uncontrollably separated from the headgear 1 and thereby be destroyed or cause damage.

The fixing gear 13 is disposed in the lower region 12 of the bracket 9 together with the bolt 14 with which the position of the spherical-head extension 11 is fixed. The padding 28 mounted on the forward end can, for example, be made of foam material and has a slide-resistant casing 40 around an inner padding 37. The casing 40 is, for example, made of silicone.

The headband 3 is rotatably attached to the forward frontal-band segment 34 by means of a connecting element 17. Padding 20 is disposed below the adjusting receptacle 18 and is built up of an inner padding 38 such as foam material and a slip-resistant casing 41 made, for example, of silicone. A slider 19 is mounted on the adjusting receptacle 18 for releasing a slip latch 46 of a gear wheel 47. The slip latch 46 is released when the slider 19 is moved. The two parts (15, 16) of the headband 3 can move out of the adjusting receptacle 18 and, in this way, the headband 3 can be enlarged to its greatest length. The two headband parts (15, 16) can be pushed into the adjusting receptacle 18 without displacing the slider 19.

The gear wheel 47 has upper and lower toothed rims (48, 49) which are separated by a holding disc-like portion 50 whereat the gear wheel 47 is held in the housing of the adjusting receptacle 18 which makes possible a rotational movement thereof. Each of the two headband parts (15, 16) is, referred to the lower toothed rim 49, provided with corresponding fitting indentations which interdigitally engage into the toothed rim 49 on opposite lying sides. With a displacement of one of the headband parts (15, 16), a corresponding displacement of the other headband part (16, 15) is simultaneously effected.

The rearward frontal-band segment 33 is rotatably attached to the forward frontal-band segment 34 with a connecting element 29. An adjusting receptacle 23 is disposed on this rearward frontal-band segment 33 in the neck region of the wearer. The diameter of the frontal band 2 can be adapted to the form of the head of the wearer by means of the adjusting receptacle 23. In order to make this adaptation, a fixing screw 32 is rotatably mounted on the adjusting receptacle 23 and is held on the adjusting receptacle by a rotatably journalled counterplate 52. A toothed rim 51 is moved with the fixing screw 32 when the latter is rotated. The two rearward frontal-band segments (30, 31) are provided with corresponding adapted indentations referred to the toothed rim 51. These indentations interdigitally engage into the toothed rim 51 on opposite lying sides. For a rotation of the fixing screw 32, a corresponding joint displacement of both rearward frontal-band segments (30, 31) is effected. A padding 22 is provided below the adjusting receptacle 23 and comprises an inner padding 39 made for example of foam material or viscose needlefelt having a slip-resistant casing 42 made for example of silicone or polypropylene.

The paddings (20, 22, 28) shown in FIG. 4 have a uniform configuration. The special advantage of these paddings is seen in that they absorb the sweat of the wearer of the headgear in an excellent manner and thereby prevent an accumulation of moisture and are very easy to remove from the headgear.

On the headgear 1 itself, the harder part of the VELCRO band is applied by adhesive at those locations at which the paddings (20, 22, 28) are located. The VELCRO band is a hook and loop fastener and is located, for example, at the interface 60 (FIG. 2) conjointly defined by padding 22 and carrier 21. (The attachment of this VELCRO band part can however also be provided with other types of known attachment devices such as fixing screws.) The other softer part of the VELCRO band having a thickness of approximately 1.5 mm is sewn to a good sweat-permeable surface casing (40, 41, 42) made of polypropylene or a material having similar material characteristics (this material can be glued selectively to the casing on the sides or can be attached to the casing according to another known technique, for example, by basting). A cotton layer is disposed on the side of the surface casing (40, 41, 42) facing away from the skin. This layer should be in the manner of terry cloth. The thickness of the surface casing (40, 41, 42) amounts to approximately 1.5 mm.

In the padding (20, 22, 28), an inner padding (37, 38, 39) is disposed made of viscose needlefelt having a thickness of approximately 2 mm (or another material having corresponding characteristics), which absorbs the moisture penetrating through the surface casing (40, 41, 42).

The constructive configuration of the paddings (20, 22, 28) makes possible that these paddings can even be washed and therefore used many times.

The thickness of the padding layers given above are exemplary and should be matched to the weight of the viewing unit 6 to be mounted in front.

The band ends (not shown) of the headband parts (15, 16) are so configured that they cannot become displaced out of the adjusting receptacle 18 in an uncontrolled manner (that is, without a conscious effort to release the same) when the slider 19 is displaced. When the headband parts (15, 16) are pushed into the adjusting receptacle 18, it is ensured that the two headband parts (15, 16) always move with the same speed in the adjusting receptacle 18 because of the configuration of the parts (15, 16) and the latching device 46 below the slider 19 so that the adjusting receptacle 18 is always located in the center of the headband 3. In this way, the padding arranged below the adjusting receptacle 18 is always ideally located on the head of the wearer and takes up part of the weight of the viewing unit 6.

Figure 5:
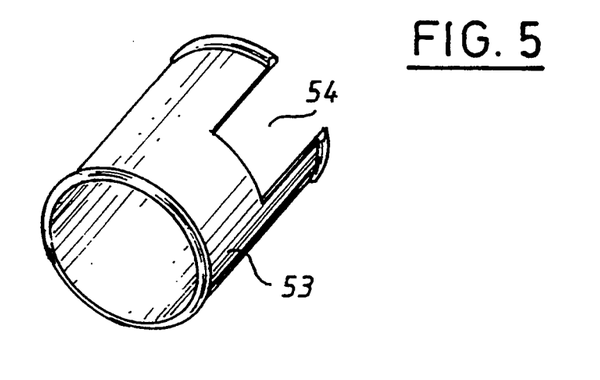
FIG. 5 is a perspective view of a protector for a prism magnifier.
Figure 6:
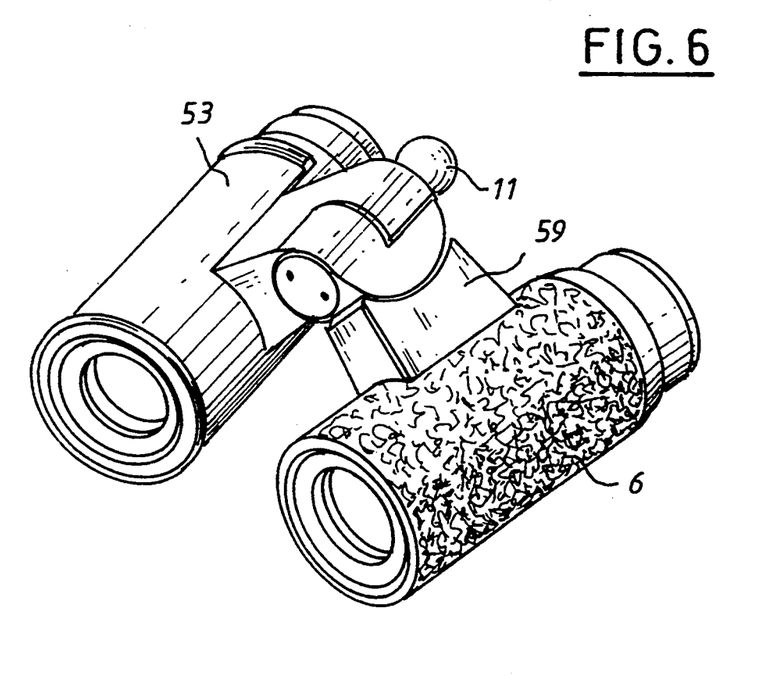
FIG. 6 is a perspective view of a prism magnifier with the protector seated thereon.

A protective cap 53 made of plastic is shown in FIGS. 5 and 6. The protective cap 53 can be pushed onto a telescope-like viewing unit 6 having two separate optics. The protective cap 53 has a tubular shape and has a cutout 54 in the region of the bridge 59 of the viewing unit 6. The protective cap 53 permits a manipulation on the viewing unit 6 without it being necessary to touch the same. This is especially very important for several medical applications wherein absolute sterility is required.

The hard-plastic casing and the frontal band can be made from an injection-molded part in an advantageous manner.

It is understood that the foregoing description is that of the preferred embodiments of the invention and that various changes and modifications may be made thereto without departing from the spirit and scope of the invention as defined in the appended claims.

What is claimed is:

1. A headgear to be worn on the head and adapted for holding a measuring unit, illuminating unit or viewing unit, the headgear comprising:

a frontal band extending around the circumference of the head of the wearer and having a front end portion;

a headband extending over the head of the wearer and having respective headband ends connected to said frontal band;

a holding device including: a base body mounted on said front end portion; a bracket having holding means for holding the unit; and, clamping means for connecting said bracket to said base body;

said base body having a slot formed therein so as to extend in a substantially vertical direction;

said clamping means including: pivot pin means defining a pivot axis and being mounted in said bracket and extending through said slot; and, manually actuable tightening means for coacting with said pivot pin means to release said bracket and permit movement of said bracket in elevation along said slot in a first line of movement relative to said base and to fix said bracket at any desired location in elevation along said slot;

said bracket being pivotally mounted on said pivot pin means so as to pivot about said pivot axis and be movable through an angular range and along a predetermined second line of movement relative to said base body while said bracket is at any location along said first line; and, detent means for latching said bracket only in a plurality of angular positions about said pivot axis within said angular range; and, said detent means including detents on said pivot pin means for fixing said positions one next to the other at predetermined intervals within said angular range; and, a resiliently-biased pressure piece mounted in said bracket for engaging any one of said detents for latching and fixing said bracket at the angular position corresponding to said one detent.

2. The headgear of claim 1, said frontal band having first and second rearward frontal band segments having respective end portions; and, an adjusting receptacle device having a housing for receiving said end portions therein; and, displacing means mounted in said housing for displacing the respective portions of said end portions in said housing relative to each other to increase or decrease the overall length of said frontal band thereby adapting said frontal band to the circumference of the head of the wearer.

3. The headgear of claim 2, further comprising first and second connecting means for rotatably connecting said headband ends to said frontal band so as to permit a rotational movement of said headband along a predetermined line of movement relative to said frontal band.

4. The headgear of claim 1, said frontal band being subdivided into a forward part having first and second ends and a rearward part having first and second ends; first connecting means for connecting said first ends together so as to permit said first ends to rotate relative to each other; second connecting means for connecting said second ends to each other so as to permit said second ends to rotate relative to each other; and, said first and second connecting means being disposed opposite each other on said frontal band so as to permit one of said parts to be rotatable relative to the other one of said segments along a predetermined line of movement.

5. The headgear of claim 4, said rearward part having first and second rearward frontal band segments having respective end portions; and, an adjusting receptacle device having a housing for receiving said end portions therein; and, displacing means mounted in said housing for displacing the respective end portions in said housing relative to each other to increase or decrease the overall length of said frontal band thereby adapting said frontal band to the circumference of the head of the wearer.

6. The headgear of claim 5, said adjusting receptacle device including an elastically bendable carrier mounted thereon; and, padding means mounted on said carrier for placement in contact with the head of the wearer.

7. The headgear of claim 1, said headband having first and second headband parts having respective ones of said headband ends; said first and second headband parts having respective free end portions facing away from said headband ends; an adjusting receptacle device having a housing for receiving said free end portions therein; displacing means mounted in said housing for displacing said free end portions relative to each other to increase or decrease the overall length of said headband thereby adapting said headband to the head of the wearer; and, latching means mounted in said housing for fixing said free end portions relative to each other when said overall length is set.

8. The headgear of claim 7, said latching means including rotatable interdigitally engaging means mounted in said housing for interdigitally engaging said free end parts; and, a slide slideably mounted in said housing for movement between a first position wherein said slide latches said interdigitally engaging means for fixing said interdigitally engaging means and said free end portions to report movement thereof and a second position when said interdigitally engaging means and said free end parts are free to move relative to each other.

9. The headgear of claim 1, further comprising a protective cap for placement on said unit when manually grasping said unit for adjusting said unit in position; and, said protective cap being made from a material which permits said protective cap to be easily disinfected, 10. The headgear of claim 1, said holding means comprising an elongated extension piece having a first end for receiving said unit thereon and a second end having a ball formed thereon; a socket opening on said bracket for receiving said ball therein so as to permit said elongated extension piece to pivot in said socket opening; and, clamping means for clamping said ball for fixing said elongated extension piece in position on said bracket.

11. The headgear of claim 1, further comprising first and second connecting means for rotatably connecting said headband ends to said frontal band so as to permit a rotational movement of said headband along a predetermined line of movement relative to said frontal band.

12. The headgear of claim 11, said frontal band being subdivided into a forward part having first and second ends and a rearward part having first and second ends; first connecting means for connecting said first ends together so as to permit said first ends to rotate relative to each other; second connecting means for connecting said second ends to each other so as to permit said second ends to rotate relative to each other; and, said first and second connecting means being disposed opposite each other on said frontal band so as to permit one of said parts to be rotatable relative to the other one of said segments along a predetermined line of movement.

13. The headgear of claim 12, said rearward part having first and second rearward frontal band segments having respective end portions; and, an adjusting receptacle device having a housing for receiving said end portions therein; and, displacing means mounted in said housing for displacing the respective end portions in said housing relative to each other to increase or decrease the overall length of said frontal band thereby adapting said frontal band to the circumference of the head of the wearer.

14. The headgear of claim 11, said headband having first and second headband parts having respective ones of said headband ends; said first and second headband parts having respective free end portions facing away from said headband ends; an adjusting receptacle device having a housing for receiving said free end portions therein displacing means mounted in said housing for displacing said free end portions relative to each other to increase or decrease the overall length of said headband thereby adapting said headband to the head of the wearer; and, latching means mounted in said housing for fixing said free end portions relative to each other when said overall length is set.

15. The headgear of claim 14, said latching means including rotatable interdigitally engaging means mounted in said housing for interdigitally engaging said free end parts; and, a slide slideably mounted in said housing for movement between a first position wherein said slide latches said interdigitally engaging means for fixing said interdigitally engaging means and said free end portions to prevent movement thereof and a second position when said interdigitally engaging means and said free end parts are free to move relative to each other.

16. The headgear of claim 11, further comprising a protective cap for placement on said unit when manually grasping said unit for adjusting said unit in position; and, said protective cap being made from a material which permits said protective cap to be easily disinfected.

17. The headgear of claim 11, further comprising an elongated extension piece having a first end for receiving said unit thereon and a second end having a ball formed thereon; said bracket having a socket opening for receiving said ball therein so as to permit said elongated extension piece to pivot in said socket opening; and, clamping means for clamping said ball for fixing said elongated extension piece in position.

18. The headgear of claim 11, said adjusting receptacle device including an elastically bendable carrier mounted thereon; and, padding means mounted on said carrier for placement in contact with the head of the wearer.

19. The headgear of claim 1, said frontal band and said headband having respective inner surfaces facing toward the head of the wearer; and said headgear further comprising: first padding means mounted on the inner surface of said frontal band at said front end portion; second padding means mounted on said inner surface of said frontal band at the neck region of the wearer; and, third padding means mounted on said inner surface of said headband.

20. The headgear of claim 19, further comprising a hook and loop fastener for each of said padding means; each of said padding means having a rearward side; said hook and loop fastener having a soft part attached to the rearward side of the padding means and a hard part attached to the inner surface of the corresponding band.

21. The headgear of claim 19, each of said padding means including a surface casing made of a material permeable to sweat; and, a material for absorbing sweat disposed within the casing.

22. The headgear of claim 21, said surface casing being made of polypropylene.

23. The headgear of claim 22, said material being made of viscose needlefelt.

24. The headgear of claim 19, further comprising an elastically bendable carrier interposed between each of said padding means and the inner surface for holding the padding means corresponding thereto.

25. The headgear of claim 19, a first carrier interposed between said frontal band at the neck region and said second padding means; said first carrier having holding means for holding the latter; and, a second carrier interposed between said headband and said third padding means; said second carrier having holding means for holding the latter; and, each of said carriers being made of a bendable elastic material.

* * * * *

UNITED STATES PATENT AND TRADEMARK OFFICE
CERTIFICATE OF CORRECTION

PATENT NO. : 5,412,811

DATED : May 9, 1995

INVENTOR(S) : Peter Hildenbrand, Walter Matuschek and Heinz Gottlob

It is certified that error appears in the above-identified patent and that said Letters Patent is hereby corrected as shown below:

In column 1, line 19: delete "headgear" and substitute -- headgears -- therefor.

In column 2, line 25: delete "is" and substitute -- are -- therefor.

In column 2, line 67: delete "the" (first occurrence).

In column 3, line 50: delete "EMBODIMENT" and substitute -- EMBODIMENTS -- therefor.

In column 7, line 8: between "made" and "for", insert -- , --.

In column 7, line 8: between "example" and "of", insert -- , --.

In column 7, line 9: between "made" and "for", insert -- , --.

In column 7, line 9: between "example" and "of", insert -- , --.

In column 8, line 2: delete "on" and substitute -- of -- therefor.

In column 9, line 59: delete "disinfected," and substitute -- disinfected. -- therefor.

UNITED STATES PATENT AND TRADEMARK OFFICE
CERTIFICATE OF CORRECTION

PATENT NO. : 5,412,811

DATED : May 9, 1995

INVENTOR(S) : Peter Hildenbrand, Walter Matuschek and Heinz Gottlob

It is certified that error appears in the above-identified patent and that said Letters Patent is hereby corrected as shown below:

In column 10, line 34: between "therein" and "displacing", insert -- ; --.

Signed and Sealed this

Fifteenth Day of August, 1995

Attest:

BRUCE LEHMAN

Attesting Officer  Commissioner of Patents and Trademarks